United States Patent [19]

Swartz

[11] 4,387,992

[45] Jun. 14, 1983

[54] ROTATABLE CUVETTE ARRAY

[76] Inventor: Peter J. Swartz, 33 Pine Ave., Randolph, Mass. 02368

[21] Appl. No.: 266,137

[22] Filed: May 22, 1981

[51] Int. Cl.³ .......................................... G01N 21/07
[52] U.S. Cl. .................................. 356/246; 356/427; 422/72
[58] Field of Search .................. 356/246, 427; 422/72

[56] References Cited

U.S. PATENT DOCUMENTS 4,226,531 10/1980 Tiffany et al. ...................... 356/246

Primary Examiner—Vincent P. McGraw
Attorney, Agent, or Firm—William Nitkin

[57] ABSTRACT

A cuvette array comprised of a boat-carrying planar disk with a plurality of boat members affixed to the disk in an annular array on one side of the disk, each boat member having a reagent supply section and a sample section, the disk having a first annular array of cuvette position identifying means and a second annular array of reagent/sample access apertures and instrument-transparent sections of the disk coinciding with portions of the cuvette sections of the boats affixed thereto.

4 Claims, 4 Drawing Figures

ROTATABLE CUVETTE ARRAY

BACKGROUND OF THE INVENTION

1. Field of the Invention

The device of this invention relates in general to rotatable disk cuvette arrays and more particularly to an improved and simplified cuvette array for use in centrifugal chemical analyzer and other instruments and machines.

2. History of the Prior Art

Rotatable cuvette arrays are well-known in the prior art and are utilized in many analyzing devices. An extensive discussion of the prior art is found in U.S. Pat. No. 4,123,173 to Bullock et al. Other pertinent disclosures of cuvette arrays are found in the following U.S. Pat. Nos.: 3,679,130 to Mayo et al 3,890,101 to Tiffany et al 3,759,666 to Hill 3,986,534 to Schmidt 3,532,470 to Rochte 3,829,223 to Hamel 3,856,470 to Cullis 3,441,838 to Moore 3,873,217 to Anderson et al 3,811,780 to Liston

SUMMARY OF THE INVENTION

It is an object of this invention to produce cuvette arrays predominantly by an injection molding process and to provide a product feasibly made by such process. This process produces a more rigid unit and may ultimately make the cost of the cuvette array much less than the cost of those produced by other methods of manufacture.

These objects are met, in accordance with the present invention, by an improved cuvette array comprising means defining a rigid planar member component thereof with upper and lower faces and a center of rotation having defined therein analyzer readable indicator means in a circular array about the center of rotation and further having defined therein substantially along radial lines with reference to the center of rotation a plurality of substantially radially elongated reagent/sample access apertures arrayed in a circular fashion with their axes defined on the radii of the planar member and further having concentric to and outward of the reagent/sample access apertures, a plurality of first analyzer-readable windows defined in the planar member, each associated with one of the reagent/sample access apertures and located respectively on the same radii of the reagent/sample access apertures axes; and means defining as further components of the cuvette array a plurality of boat members, each having elongated opposing side walls, an outer end wall and an inner end wall joined to the side walls, all the walls having upper rims joined in a fluid-tight fashion to the planar disk, and a base having integrally formed therein and in the adjoining side walls a divider of ramp form defining with the walls and base a reagent chamber on a radially inner side thereof and a sample chamber on the radially outer side thereof, each boat member located beneath a reagent/sample access aperture having its reagent chamber directly below said reagent/sample access aperture and its sample chamber accessible through the reagent/sample aperture and below the first clear optical window, each boat having a clear section in its base below its respective optical window, the planar member and boat components being constructed and arranged for weldability at a closed figure at the upper walls of the rim of each boat to the planar member; and the thickness of each of the planar members to boat walls being in ratio between 1:2 to 2:1 and each member and walls being within 0.020 to 0.070 inch average thickness.

In order to effectively provide such an assembly, the disk and boats should be made of the same or weld-compatible plastic materials of similar thickness. Each should have an average wall thickness of 0.020-0.070 inch and be in a thickness ratio between 1:2, 2:1 (disk thickness; boat wall) with respect to each other. While the boat base should preferably fall in the same thickness range as the boat walls, considerably more leeway can be afforded to the base.

The boat walls should terminate in upper rims of generally flat, but having a bead therof, form which can be pressed and vibrated ultrasonically in contact with the disk to form leak-tight durable welds over a continuous closed figure boat-disk interface without cracking any boat portion or the disk region around the access aperture confronting the boat. In some embodiments though the closed figure welding may be unnecessary as the leak-tight seal may only be formed around the upper rim of the outer end of the boat where the reagent/sample mixture is thrown while the disk is spinning.

Locating means are provided to rapidly align the boats with and in proper relation to confronting apertures prior to welding. Ultrasonic welding is carried out at high speed.

Further objects of the present invention include provision of a simplified cuvette array that can be reused if desired, availability to use less reagent than cuvette arrays of the prior art, and/or other objects apparent from the following disclosure, singly or in combination.

DESCRIPTION OF THE PREFERRED EMBODIMENT(S)

Figure 1:
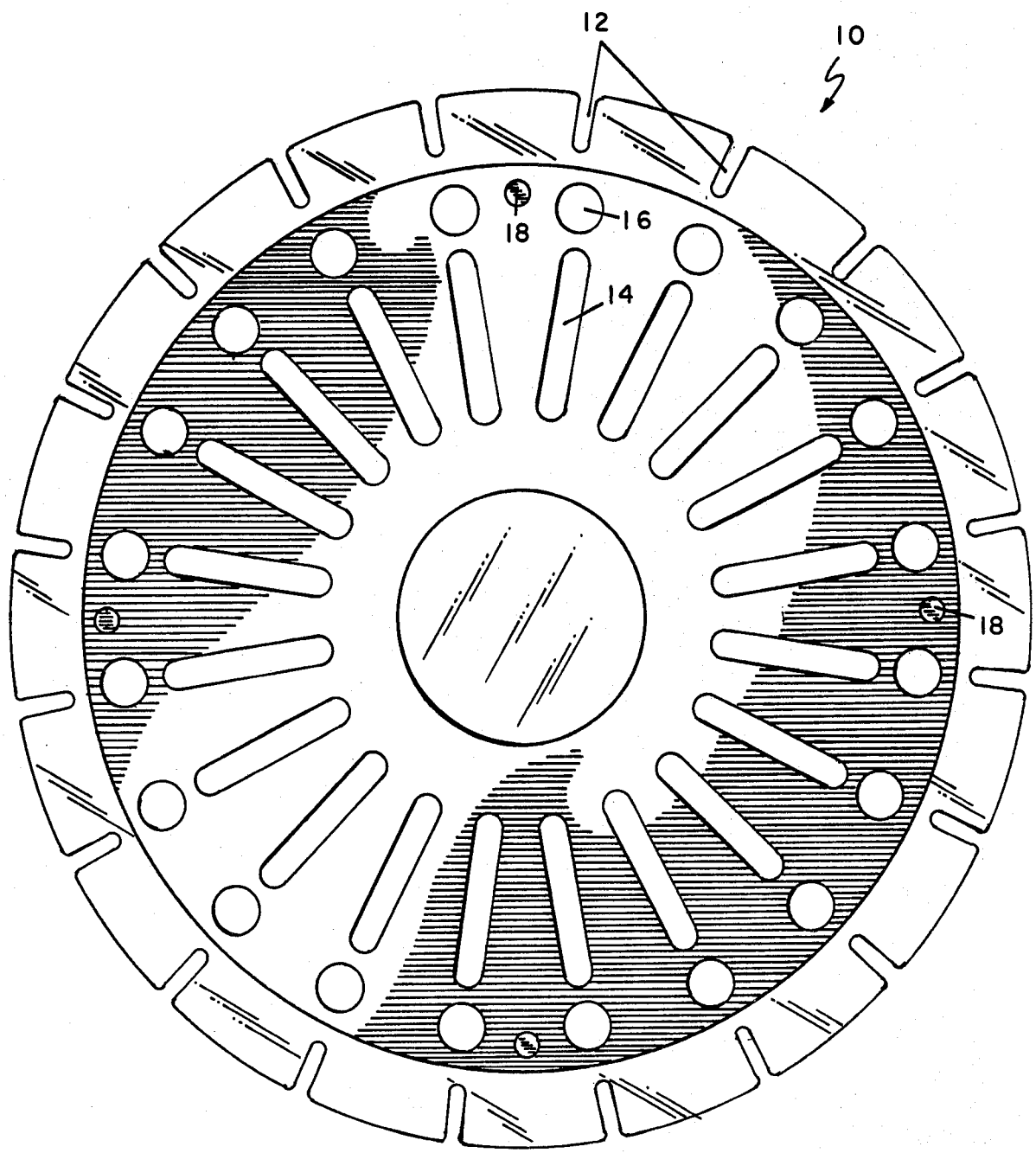
FIG. 1 illustrates a top view of the cuvette array of a preferred embodiment of this invention.

FIG. 1 illustrates a top view of the preferred embodiment of this invention which is comprised of a circular planar member 10 disk which is injection molded of a polystyrene material having a thickness of approximately 0.050 inch. Arrayed on its upper surface in circular configuration are a plurality, and in this illustrated preferred embodiment, a series of 20 reagent/sample access apertures 14 which are elongated rectangular (preferably not elliptical) openings with rounded ends aligned with their long axes on radii of the circular planar member. Reagents and samples are inserted by pipettes through the apertures into the reagent (outer) and sample (inner) sections of the boats which can be mounted on the disk in alignment with the apertures to form a complete assembly which process and assembly will be described in further detail below. Arrayed in an outer circle of the disk are a series of as-molded first optical windows 16, each associated with one of said reagent/sample access apertures 14 on its radii. These windows are clear portions defined within the substantially opaque material of planar member 10. Windows 16 allow a centrifugal chemical analyzer in which the disk is loaded in per se conventional fashion of the art to read the reaction. A series of reference notches 12 are arrayed around the perimeter of planar member 10, the rim being composed of clear plastic. The notches help to identify the position of the cuvettes so that they can be read by the analyzer. A series of locating pins are provided to assist in the positioning of an annular component over the array which component many of the prior art analyzing devices utilize to assist in aligning the array within the analyzer.

Figure 2:
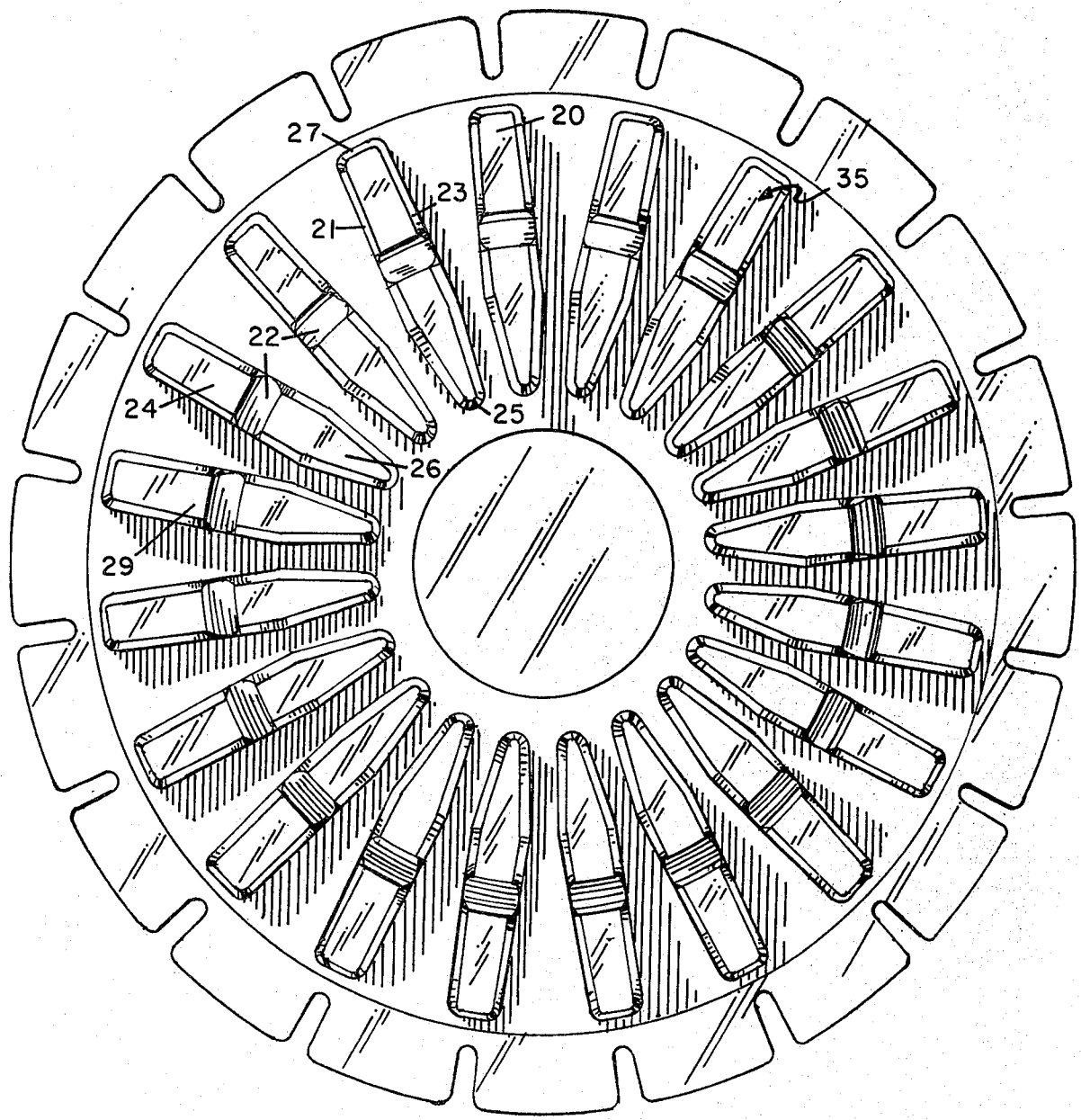
FIG. 2 illustrates a bottom view of the cuvette array of a preferred embodiment of this invention.

FIG. 2 is a bottom view showing planar member 10 with a series of boat members 35 arrayed around the bottom thereof. Each boat member has elongated side walls 21 and 23 with an inner end 25, outer end 27, and a base 29 with ramp 22 formed integrally as a part of the base and side walls separating an inner reagent supply chamber section 26 from an outer sample (cuvette) chamber section 24. Each injection molded boat member has walls approximately 0.042 inch thick and is ultrasonically welded as described below to the planar disk beneath a reagent/sample access aperture with its sample chamber beneath said first optical window. When inserting the reagent through the reagent/sample access aperture by pipette, one inserts the reagent into the reagent chamber and the sample into the sample chamber. An optically clear section 20 is located in the base of each boat member 35 in vertically opposing position to the first optical window 16 of planar member 10 so that the analyzer can detect the contents therethrough of the sample chamber aligned therewith. In one embodiment the entire base may be optically clear. The shape of at least the inner third (radially) of each boat tapers toward the center of the disk so that each boat may be properly positioned in a circular array without contacting one another. The boat members, or at least the reagent supply sections thereof, are also constructed in such a narrow configuration overall so that they are adapted to hold in the range of 350 microliters to 1 milliliter.

It is desirable to maintain such narrow configuration so that the volume of reagent used for analysis is kept small consistent with reliable analysis. Ramp 22 must not reach all the way up to contact planar member 10 because when the cuvette array is spun, the reagent, by centrifugal force, must travel over the ramp and mix with the sample in the sample chamber. It is important that the reagent access aperture be just large enough to allow the pipettes delivering the samples and reagents into their respective chambers but narrow and short enough to prevent fluid from splashing back out therethrough when the device is in use. An aperture approximately 1 inch in length and approximately 3/16 inch in width with its outer end extending beyond ramp 22 approximately 1/16 inch has been found to work well in conventional centrifugal analyzers of today's art at speeds of 100 rpm to 500 rpm and acceleration/deceleration and vibration and rigidity of mounting conditions currently prevalent.

Figure 3:
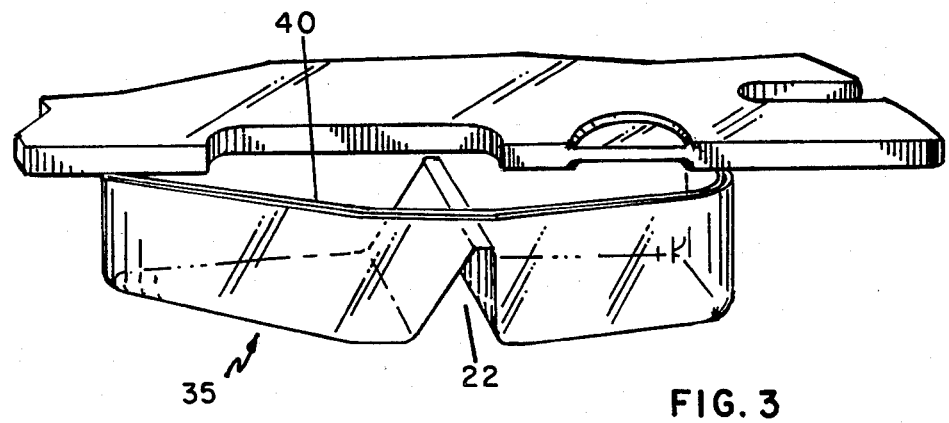
FIG. 3 illustrates a sector-shaped section of the cuvette array in cutaway view showing the interior of a boat member component thereof.

FIG. 3 shows a cutaway view of a section of single boat member 35 showing ramp 22 over which the reagent must flow when the array is spun in the analyzer causing it to mix with the sample within the sample chamber and then be read by the analyzing device.

Figure 4:
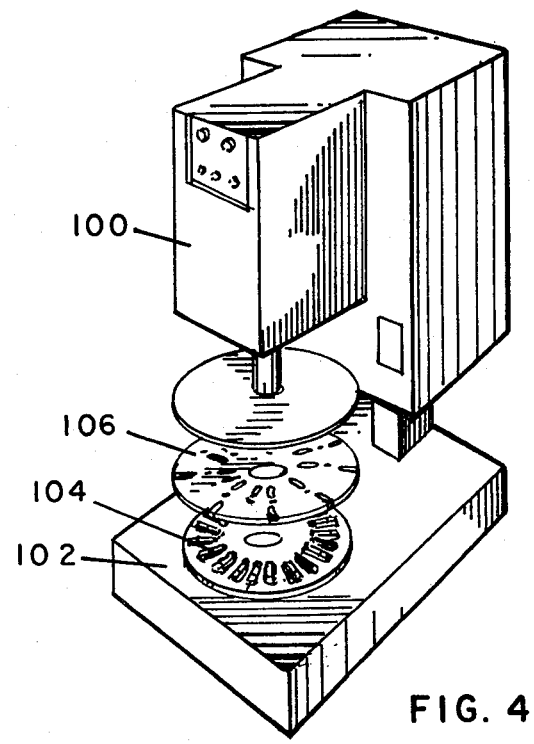
FIG. 4 illustrates ulltrasonic welding machine preferably, and with distinct advantage, used in the method of manufacture of FIGS. 1-3 devices or the like in accordance with a preferred embodiment of the process of the present invention.

FIG. 4 illustrates an ultrasonic welding machine 100 showing a boat nest fixture 102 with boats 104 in place therein and with disk 106 shown suspended thereabove. The injection molding of all twenty-one parts of the disk helps to produce a rigid product. In the injection molding process the first clear optical windows are all depressed on their upper and lower surfaces 0.002 inch from the face of the disk so that they will not be scratched during the assembly process. Each boat is molded having a bead 40 on its upper edges of its open side so that when placed into nest 102, which exactly positions each boat, the disk can be accurately positioned and referenced and ultrasonically welded to the boats in one operation by the ultrasonic welding machine 100, which machines are well-known.

Although the present invention has been described with reference to particular embodiments, it will be apparent to those skilled in the art that variations and modifications can be substituted therefor without departing from the principles and spirit of the invention.

I claim:

1. An improved cuvette array comprising:

a. means defining a rigid planar member component thereof with upper and lower faces and a center of rotation having defined therein analyzer readable indicator means in a circular array about said center of rotation and further having defined therein substantially along radial lines with reference to said center of rotation a plurality of substantially radially elongated reagent/sample access apertures arrayed in a circular fashion with their long axes defined on said radii of the planar member and further having, concentric and outward of the reagent/sample access apertures, a plurality of first analyzer-readable windows defined in said planar member, each associated with one of said reagent/sample access apertures and located respectively on the same radii of said reagent/sample access apertures' axes;

b. means defining as further components of the cuvette array a plurality of boat members, each having elongated opposing side walls, an outer end wall and an inner end wall joined to said side walls, all said walls having upper rims joined in a fluid-tight fashion to said planar disk, and a base having integrally formed therein an in said adjoining side walls a divider of ramp form defining with said walls and base a reagent chamber on a radially inner side thereof and a sample chamber on the radially outer side thereof, each boat member located beneath a reagent/sample access aperture having its reagent chamber directly below said reagent/sample access aperture and its sample chamber accessible through said reagent/sample aperture and below said first clear optical window, each of said boats having a a clear section in its base below its respective optical window;

c. the said planar member and boat components being constructed and arranged for weldability at the upper walls of the rim of each boat to the planar member; and d. the thickness of each of the planar members to boat walls being in ratio between 1:2 to 2:1 and each of the planar members and walls being within 0.020 to 0.070 inch average thickness.

2. The cuvette array of claim 1 wherein said positioning of said plurality of boat members under said reagent/sample access apertures is such that the reagent/sample access apertures are predominantly over said reagent chambers and only a portion of the access apertures extends over said ramps and said sample chambers which is sufficient for the insertion of a pipette into said sample chambers, i.e. substantially pipette-sized portion) and wherein said reagent/sample access apertures are narrower than the separation of said boats' side walls to help to prevent spillage of reagent from out of said boats when the cuvette array is in use.

3. The cuvette array of either of claims 1 or 2 wherein the radially innermost portions of each boat's side walls converge towards each other to define a tapering of the boat's radially innermost portion limiting the amount of reagent storable in the reagent portion of such boat and allowing a higher number of boats to be clustered annularly and extend inwardly towards said center of rotation to an extent consistent with high stiffness of the assembly as a whole through such placement, number and wall thickness of the boats.

4. The cuvette array of claim 3 wherein said first optical windows are thinner than the thickness of said planar members.

* * * * *